Figure 1:
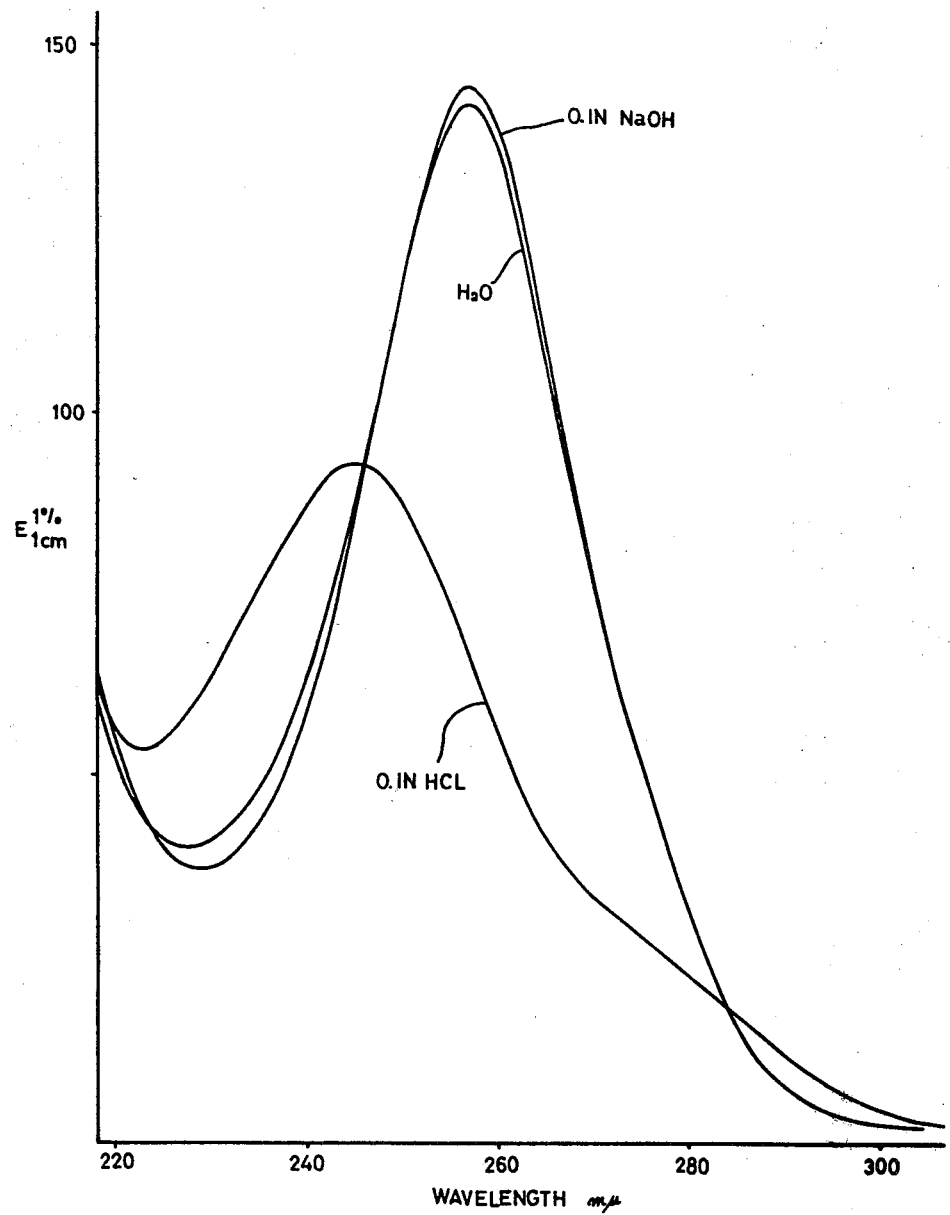

United States Patent [19] [11] 3,949,070
Arai et al. [45] Apr. 6, 1976

[54] NEW ANTIBIOTIC SUBSTANCE, ITS PREPARATION AND ITS USE AS GROWTH PROMOTING AGENTS

[75] Inventors: Mamoru Arai; Akio Torikata; Hisayoshi Fukatsu; Noritoshi Kitano; Toshiaki Matsuzawa, all of Hiro, Japan

[73] Assignee: Sankyo Company Limited, Tokyo, Japan

[22] Filed: Jan. 30, 1975

[21] Appl. No.: 545,391

Related U.S. Application Data

[62] Division of Ser. No. 480,514, June 18, 1974.

[30] Foreign Application Priority Data
June 30, 1973 Japan................................ 48-73807

[52] U.S. Cl. .............................................. 424/118
[51] Int. Cl.² ........................................ A61K 35/00
[58] Field of Search .................................. 424/118

[56] References Cited
UNITED STATES PATENTS
3,689,640   9/1972   Shahani et al. ...................... 424/118

Primary Examiner—Jerome D. Goldberg
Attorney, Agent, or Firm—Flynn & Frishauf

[57] ABSTRACT

Antibiotic substance named "Pholipomycin" which is useful as a growth promoting agent for domestic animals, poultries and the like and produced by the cultivation of a new microorganism, *Streptomyces lividoclavatus* strain No. 3176, NRRL 8022.

5 Claims, 2 Drawing Figures

NEW ANTIBIOTIC SUBSTANCE, ITS PREPARATION AND ITS USE AS GROWTH PROMOTING AGENTS This is a division, of application Ser. No. 480,514, filed June 18, 1974, which has been allowed.

This invention relates to a new antibiotic substance, a process for the production thereof and its use as a growth promoting agent for animals.

More particularly, it is concerned with a new antibiotic substance named "Pholipomycin", a process for the production thereof by the use of a new strain belonging to the genus Streptomcyces and its use as a growth promoting agent for various animals such as domestic animals, poultries and pet animals.

We have found that a new antibiotic substance, pholipomycin, is produced in a cultured broth of Streptomyces lividoclavatus strain No. 3176 which was isolated from a soil sample collected at Obana, Tochigi Prefecture, Japan and also that this new antibiotic substance shows a highly potent growth promoting effect on various animals such as domestic animals, poultries, pet animals and the like.

Heretofore, some antibiotic substances such as chloramphenicol, aureomycin and the like have been administered to the animals in order to accomplish prophylactic treatment of various diseases in, for example, domestic animals, poultries and the like, simultaneously with improvement in fattening, growth promotion and feed conversion rate. However, these prior antibiotic substances have been found to have some disadvantages in that they tend to remain in animal products such as eggs, meats and the like and that microorganisms resistant to these drugs could be found. Under such circumstances, development of a new drug capable of being less adsorbed from the gastrointestinal tract of animals has been earnestly desired in the art.

The present antibiotic substance is exremely useful in the practical aspect of food hygiene, since it has been found to be less adsorbed in intestines when orally administered.

It is, accordingly, a primary object of this invention to provide a new antibiotic substance, pholipomycin, which is useful as a growth promoting agent for the animals.

Another object of this invention is to provide a process for the production of pholipomycin by the use of a newly discovered microorganism, Streptomyces lividoclavatus No. 3176.

Still another object of this invention is to provide a new use of the present antibiotic substance as a growth promoting agent for the animals.

Other objects and advantages of this invention will be obvious from the following detailed description.

Morphological characteristics of the above pholipomycin-producing strain No. 3176 are as follows:

1. When observed under a microscope, aerial mycelium is well-branched and long aerial hyphae extends. Aerial hyphae is sympodially branched, but no spirals and conidia chain are observed. Spores are spherical to elliptical and 0.6 ~ 0.8 × 0.8 ~ 1.1 $\mu$ in size. Spore surface is smooth. Spore chains are in 10 – 50 spores per spore chain and characterized by short and clavate side branch which is formed with 2 – 3 spores. No flagellate spore and sporandium are formed and sporophores are on aerial mycelium.

2. Results obtained in the culture on various culture media (observation made after a two-week cultivation at 28°C unless otherwise stated) are as shown in Table 1.

Table 1

| Medium | Growth | Aerial mycelium | Substrate mycelium | Reverse | Soluble pigment |
|---|---|---|---|---|---|
| Sucrose-nitrate agar | Moderate | Scant, white | Scant, white | White | None |
| Glucose-asparagine agar | Good | Scant, bluish gray | Scant, white | Bluich gray | do |
| Glycerol-asparagine agar | Good | Scant, bluish gray | Abundant, dull orange | Dull orange | do |
| Inorganic salts-starch agar | Good | Moderate Bluish gray | Moderate, Pale yellowish brown | Pale yellowish brown | do |
| Tyrosine agar | Good | Scant, bluish gray | Moderate, light brownish gray | Light brownish gray | Scant, brownish gray |
| Nutrient agar medium | Good | Scant, white | Scant, pale yellowish brown | Pale yellowish brown | None |
| Yeast extract-malt extract agar | Abundant | Abundant, bluish gray | Abundant, light brownish gray | Light brownish gray | do |
| Oatmeal agar | Moderate | Moderate, pale yellowish orange | Abundant, pale yellowish orange | Pale brown | do |

3. Physiological properties of the strain No. 3176 are shown in Table 2.

Table 2

Temperature range for growth: 10~37°C.
Gelatin liquefaction (18°C.): weak
Starch hydrolysis: weak
Milk coagulation: 25°C., −

Table 2-continued

| | |
|---|---|
| Milk peptonization: | 25°C., + (pH 6.4) |
| Melanin formation | + (in tyrosine-agar medium) |
| | − (in peptone-yeast extract iron agar medium) |
| | − (in "Triptone-Bacto"*-yeast extract broth) |
| Nitrate reduction: | + |

*Trade name, Difco Laboratories, U.S.A.

4. Carbon source utilization pattern of the strain No. 3176 on Pridham-Gottlieb's agar medium is shown in Table 3.

Table 3

| | | | |
|---|---|---|---|
| L-arabinose | − | Inositol | ++ |
| D-xylose | − | L-rhamnose | ++ |
| D-glucose | ++ | Raffinose | ++ |
| D-fructose | ++ | D-mannitol | − |
| Sucrose | ++ | | |

From the summary of the above properties, the strain No. 3176 belongs to the genus *Streptomyces*, its aerial mycelium is sympodially branched and bluish gray on most of the media. Also, its spores are spherical to elliptical and its spore surface is smooth. In particular, its most marked characteristics are in that it has spore chain with short and clavate side branches which form 2 ~ 3 spores.

Searching the known strains having the above properties, as the most closely related strain in view of spore forming may be mentioned *Streptomyces clavuligerus* which was described in the International Journal of Systematic Bacteriology, Vol. 21, No. 4, 326 ~ 331 (1971). However, this known strain is distinctly different from the strain No. 3176 in that the former has rectangular to cylindrical spores and its aerial mycelium is pale yellowish green on many media and that the former does not utilize such carbon sources as D-glucose, D-fructose, sucrose, L-rhamnose, raffinose and the like. From the above comparative studies, it can be clearly concluded that the present strain is distinctly different from *St. clavuligerus*.

From the above, the strain No. 3176 has been identified as a new species and named *Streptomyces lividoclavatus* strain No. 3176. The strain No. 3176 has been deposited under an accession No. 2101 with Technical Research Institute of Microbial Industry, Agency of Industrial Science and Technology, Ministry of International Trade and Industry, Japan, and also as NRRL-8022 in the Northern Regional Research Laboratory, Northern Central Region, Agricultural Research Service, United States Department of Agriculture, at Peoria, Illinois, U.S.A. Although has been explained the strain No. 3176 in the foregoing, it is well-known that various properties of Streptomyces are not definite, but may easily be varied naturally and artificially. The strains which may be employed in this invention include all of the strains which belong to the genus Streptomyces and are capable of producing pholipomycin.

Cultivation in the process of this invention may be carried out according to the method generally employed for Streptomyces. Shaken culture or submerged culture in a liquid medium is preferable.

As medium components may be employed any of the well-known nutrient materials for Streptomyces. For instance, as an assimilable carbon source, glucose, glycerol, maltose, dextrin, starch, lactose, sucrose, molasses, soybean oil, cotton seed oil, etc. and, as an assimilable nitrogen source soybean meal, peanut meal, cotton seed meal, fish meal, corn steep liquor, peptone, meat extract, yeast, yeast extract, sodium nitrate, ammonium nitrate, ammonium sulfate, etc. may be used. And, sodium chloride, phosphates, calcium carbonate, etc. may be used as an inorganic salt. A minor amount of a metal salt may also be added, if necessary.

In carrying out liquid cultivation with aeration and agitation, an anti-foaming agent, e.g., silicone oil, vegetable oils, surfactants, etc. may be suitably employed.

The pH of the medium may be suitably within or around neutral range and cultivation temperature may be usually of 25 ~ 30°C., in particular about 27°C. being preferred.

Change with time lapse in the activity of an antibiotic substance pholipomycin, which is being produced in the cultured broth as the cultivation proceeds, can be determined by a wellknown cylinder-plate test method using *Staphylococcus aureus* 209P as a test microorganism. Usually, the maximum production of pholipomycin may be accomplished by cultivation for about 96 ~ 240 hours.

Pholipomycin is predominantly in a solid portion of the cultured broth.

Pholipomycin may be recovered from the cultured broth by various methods which are well-known in the art for the recovery of antibiotic substances. For instance, after completion of the cultivation, the cultured broth is made acidic by the addition of a suitable acid, filtered with a filter aid such as diatomaceous earth and the like to collect mycelium and other solid mass containing diatomaceous earth in which pholipomycin is involved due to its rather sparing solubility in water under acidic condition, and the so gathered mass is extracted with a watermiscible solvent such as, for examples, acetone, methanol or a mixture thereof to recover the desired pholipomycin.

On the other hand, the pholipomycin existing in the filtrate of the cultured broth or the residual liquid obtained after distillation of the organic solvent from the mycelium extract, may be recovered by the extraction with a water-immiscible organic solvent such as n-butanol under acidic condition.

The so obtained extract containing pholipomycin is subjected to distillation under reduced pressure, passed through a layer of an anion exchange resin so that pholipomycin is adsorbed thereupon because of its inherent acidity, and then the adsorbed pholipomycin may be eluted with a suitable eluant. In some cases, the extract may be passed through a layer of a cation exchange resin to remove basic impurities.

As examples of the anion exchange resins may be strongly basic anion exchange resins, e.g., Dowex IxI (manufactured by Dow Chemical Co.), etc., but weakly basic anion exchange resins, e.g., Duolite A-2 (manufactured by Diamond-Alkali Co., U.S.A.) may be preferably employed.

Examples of the cation exchange resin which may be employed are strongly acidic cation exchange resins, e.g., Dowex 50W × 4 (manufactured by Dow Chemical Co., U.S.A.), Amberlite IR-120 (manufactured by Rohm and Haas Co., U.S.A.) and the like.

And, a chromatography for further purification of pholipomycin may be effected by the use of silica gel, Avicel (microcrystalline form of cellulose, available from Asahi Kasei Kogyo K.K., Japan), diethylaminoethyl cellulose (an anion exchange cellulose, available from Serva Feinbiochemica, West Germany) and the like.

Further, pholipomycin may be purified by the use of such procedures as dialysis for removing low molecular impurities in view of high molecular substance pholipomycin itself, gel filtration with Sephadex G-50 (available from Pharmacia Fine Chemical A.B., Sweden) and the like.

Then, the aqueous solution containing the pholipomycin so extracted and purified is concentrated, and freeze-dried or to the solution is added a water-miscible organic solvent such as acetone and the like to precipitate the desired antibiotic substance, thereby yielding the pure pholipomycin as white powders. Physicochemical properties of pholipomycin are given below.

1. Appearance White powder
2. Melting point No clear melting point with gradual brown coloring at 250°C. or higher
3. Elementary analysis C : 50.15 % H : 7.14 % N : 5.48 % S : 2.33 %
4. Molecular weight 5100; found by a gel-filtration method using Sephadex G-100 in a 0.05 M phosphate buffer solution having pH 7.0.
5. Specific rotation $[\alpha]_D^{20} = +6.0°$ (C = 1 cm., $H_2O$)
6. Ultraviolet absorption spectrum As shown in FIG. 1 values of maximum absorption positions and of $E_{1\%}^{1\ cm}$ are as shown in Table 4.

Table 4

| Solvent | Absorption Max. (mμ) | $E_{1\ cm}^{1\%}$ |
|---|---|---|
| $H_2O$ | 257 | 142 |
| 0.1N HCl | 245 | 93 |
| 0.1N NaOH | 258 | 144 |

Figure 2:
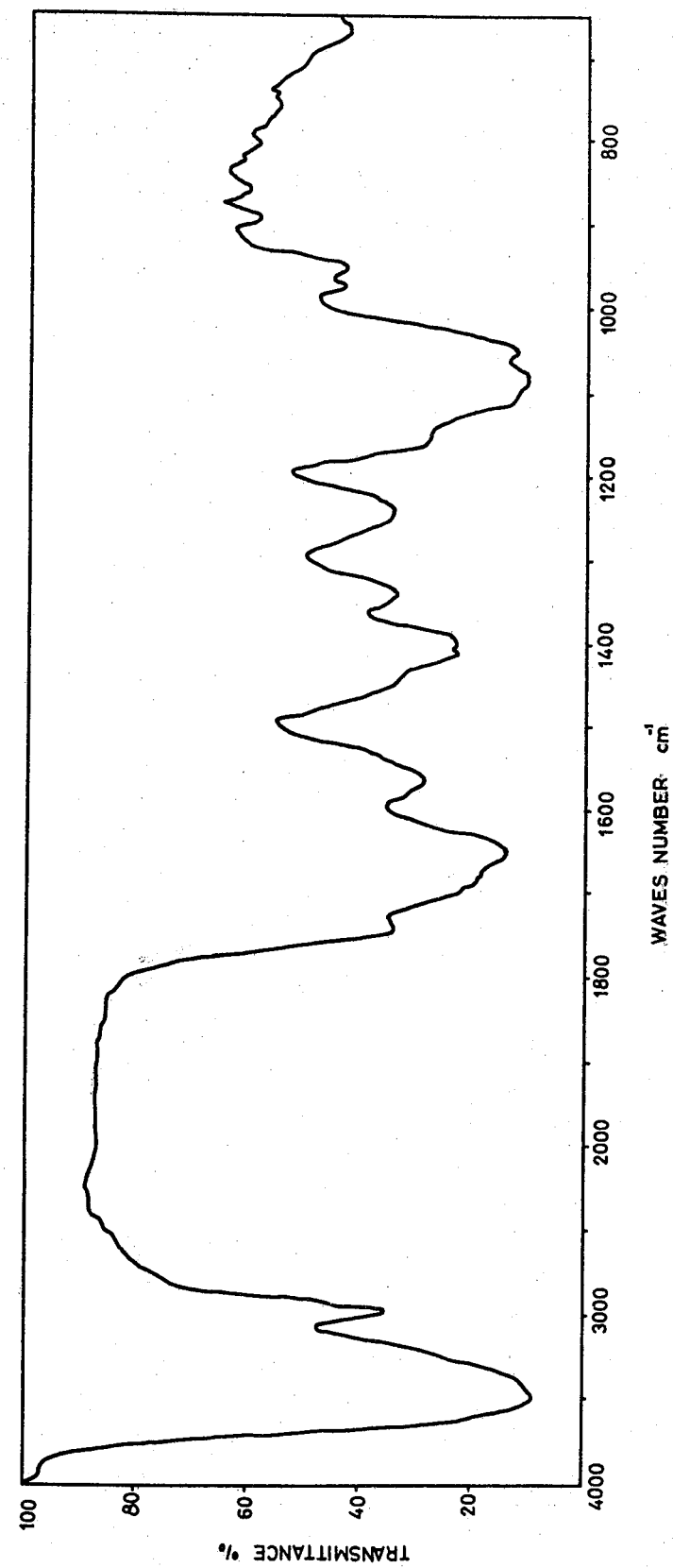

7. Infrared absorption spectrum As shown in FIG. 2 (measured in KBr pellet)
8. Neutrality, basicity or acidity Acidic substance (pKa = 4.37, 9.43 $H_2O$)
9. Solubility It is easily soluble in water, soluble in methanol and n-butanol, sparingly soluble in acetone, chloroform and ether.
10. Color reaction Positive for Tollens reaction. False positive for Elson-Morgan reaction. Negative for ninhydrin, Benedict, biuret, Bial, ferric chloride and anthrone reactions. When heating with pyridine, ninhydrin reaction is changed positive.
11. Stability Its aqueous solution is extremely stable at pH 4 ~ 10. 100 %, 90 % and 90 % of its activity remain unchanged at pH 6 ~ 8, even pH 4 and 10, respectively, after heating its aqueous solution of 200 μg./ml. of pholipomycin at 60°C. for 30 minutes.
12. Thin-layer chromatography By a thin layer chromatography (ascending method) using Cellulose.-Chromatogram Sheet 6065 (manufactured by Eastman Kodax Co., U.S.A.) and Silica Gel (Sheet) Chromatogram 6060 (manufactured by Eastman Kodak Co.), Rf values are 0.74 and 0.25 in n-propanol-2NNH$_4$OH (7:3) respectively. As a detection method is employed a bioautography with Staphylococcus aureus 209p or a U.V. absorption method.

Biological activities of pholipomycin are set forth below.

1. Antimicrobial spectrum Minimal inhibitory concentrations of various microorganisms are as shown in Table 5.

Table 5

| Test organism | MIC (μg./ml.) | |
|---|---|---|
| | Medium A | Medium B |
| Staphylococcus aureus 209P JC-2 | 0.39 | 0.09 |
| S. aureus 56 (multi-resistant) | 0.39 | 0.19 |
| S. aureus 193 (multi-resistant) | 0.39 | 0.19 |
| | 50 | 0.09 |
| Bacillus subtilis PCI 219 | — | |
| Sarcina lutea PCI 1001 | >100 | 12.5 |
| Corynebacterium xerosis B58-3 | >100 | 100 |
| Escherichia coli NIHJ JC-2 | 50 | 25 |
| E. coli K-12 | 12.5 | 12.5 |
| E. coli (ST resistant) | 25 | 25 |
| Pseudomonas aeruginosa B-1-1 | 3.12 | 0.78 |
| P. Sp. SC-8328 | 100 | 25 |
| Proteus vulgaris B-30-8 | 0.78 | 3.12 |
| Klebsiella pneumonia PCI 602 | 25 | 12.5 |
| Aeromonas liquefacieus Y-62 | 0.78 | 0.39 |
| Mycobacterium smegmatis ATCC 607 | 50 | — |

| | Medium C |
|---|---|
| Candida albicans YU 1200 | >100 |
| Saccharomyces cerevisiae ATCC 9763 | >100 |
| Trichophyton mentagrophytes F 63-9 | >100 |
| Fusarium moniliforme IAM 5062 | >100 |
| Piricularia oryzae IAM 5087 | >100 |

Medium A: Nutrient agar with 1 % glycerol
Medium B: Heart infusion agar
Medium C: Sabouraud dextrose agar
Cultivation: MIC was determined after incubation for 24 hours at 37°C. (for 48 hours with regard to the Mycobacterium smegmatis) for bacteria and for 48 hours at 28°C. for yeasts and fungi.

2. Toxicity $LD_{50}$ of pholipomycin to mice by intravenous injection is 600 – 800 mg./kg. No abnormal phenomenon in a fish toxicity test with killifish has been observed in a bath of 200 ppm. of pholipomycin.

3. Protective activity Pholipomycin has been observed to show an effectiveness in a protection test on mouse by Staphylococcus aureus. More specifically, RFVL strain mice of each average body weight of about 20 g., each group consisting of 5 animals, were inoculated with 1 × 10$^7$ cells per mouse of Staphylococcus aureus No. 42, a multi-resistant strain, and pholipomycin was subcutaneously administered in its sterile sodium chloride solution at 50, 100 and 200 mg./kg. two times, namely, immediately after the inoculation and after 4 hours from the inoculation. The numbers of surviving mice were 0, 1 and 5, respectively.

As is apparent from the above items (1) through (3), pholipomycin has a strong antibacterial activity against gram-positive and -negative bacteria and, in particular, it is highly effective against various resisant microorganisms and extremely low in its toxicity. Accordingly, the present antibiotic is also useful as a medicaments for human beings.

From the results of our studies on known antibiotic substances having the above-described physico-chemical and biological properties, it has been confirmed that the pholipomycin of this invention is believed to be closely similar to those antibiotics substances such as macarbomycin, diumycin A and moenomycin.

However, it should be noted that the present pholipomycin is different from the above-listed known antibiotic substances with regard to the points as indicated below.

1. Physico-chemical properties Comparison of Physico-chemical properties of pholipomycin and the above-listed known antibiotic substances are summarized in Table 6.

Table 6

| Properties | Pholipomycin | Moenomycin A | Moenomycin C | Moenomycin D | Macarbomycin | Diumycin A |
|---|---|---|---|---|---|---|
| m.p. (dec.) | 250°C | | | | 190 – 200 | 251 – 257 |
| Analysis (%) | $-NH_4$ | | | $-Na$ | $-NH_4$ | Na |
| C | 50.15% | 48.6% | 49.1% | 43.7% | 47.35% | 48.65% |
| H | 7.14 | 7.2 | 7.4 | 7.1 | 7.25 | 5.42 |
| N | 5.48 | 5.3 | 5.3 | 5.7 | 4.90 | 4.00 |
| P | 2.33 | 1.8 | 1.7 | 1.9 | 2.12 | 1.91 |
| Empirical formula | $C_{50-65}H_{85-111}N_{5-6}O_{25-35}P$ | $C_{70}H_{124}N_6O_{46}P$ | $C_{75}H_{135}N_7O_{42}P$ | — | $C_{68-79}H_{125-144}N_{6-7}O_{41-46}P$ | $C_{68-72}H_{93-107}O_{38-40}Na_6$ |
| UV ($m\mu$, $E^{1\%}_{1cm}$) $H_2O$ | 257  142 | 258  106 | | | 258 | 0.1N KOH |
| 0.1N NaOH | 258  144 | 258  106 | | | −259  120 | 257  120 |
| 0.1N HCl | 245  93 | 246  78 | | | 246  70, −247 | 246  78 |
| $[\alpha]_D$ | +6.0°(C=1 $H_2O$) | | | | +15°(C=1 MeOH) | +8.0°(C=1 $H_2O$) |
| Glucosamine | + | + | + | + | + | + |
| Quinovosamine | − | + | + | + | − | − |
| Glucose | − | + | + | + | + | + |
| TLC * | 0.53 | 0.61 | 0.73 | | 0.43 | 0.39 |

* EtOH-concNH₃-H₂O (8:1:1)
Four times multi-development on Silica gel chromatogram sheet 6060.

As is apparent from the Table 6, pholipomycin is distinctly different from the macarbomycin, diumycin A and moenomycins in that pholipomycin does not contain glucose as its constitutive sugar but all the known antibiotics contain glucose as their constitutive sugars, while it is similar to the known antibiotics in other aspects. Analysis of constitutive sugars is effected by hydrolysis of each antibiotic substance in 2N hydrochloric acid at 105°C. for 3 hours and subsequent paper chromatography of the hydrolysate (n-butanol-pyridine-water, 6:4:3, descending method for 20 hours).

As the other known antibiotic substances which are believed to be similar to the present pholipomycin, are mentioned prasinomycins A, B and C, moenomycins E, F, G and H, diumycin B, 19402RP, 8036RP, 11837RP and the like. These antibiotics are, however, distinctly different from pholipomycin in many aspects, more illustratively, the prasinomycins being soluble in chloroform, the 19402RP containing sulfur atom and others having no maximum absorptions in their UV spectra, which are distinctly different from pholipomycin.

2. Comparison tests of antibacterial activity Activity of each antibiotic was tested by cylinderplate method using 12.5, 50 and 200 μg/ml of the antibiotic in M/15, pH 7.0 phosphate buffer. Percent activity was calculated using pholipomycin as a standard antibiotic. The results are summarized in Table 7.

Table 7

| | Pholi-pomycin | Macarbomycin | Diumycin | Moenomycin (A + C) |
|---|---|---|---|---|
| S. aureus 209P | 100 | 164 | 99.3 | 131 |
| E. coli NIHJ | 100 | 16.2 | 11.6 | 37.0 |
| P. aeruginosa B-1-1 | 100 | 35.7 | 27.7 | 48.3 |

As is apparent from the Table 7, pholipomycin is different from the above-mentioned antibiotic substances, which have similar physico-chemical properties, in antibacterial activity and spectrum. Especially, pholipomycin has a characteristic of a potent antibacterial activity against gram-negative bacteria.

As the comparative studies on the aforesaid physico-chemical and biological properties, it will be fairly concluded that the present pholipomycin is clearly distinguishable or different from other known antibiotic substances and thus a novel antibiotic substance.

The references about the antibiotic substances as described above are as follows:

1. Moenomycins A, C, D, E, F, G and H: Antimicrobial Agents and Chemotherapy-1965, 734 ~ 736, 737 ~ 742 (1966) and Journal of Antibiotics, 22, 12, 597 ~ 602 (1969).
2. Macarbomycin: Journal of Antibiotics, 23, 1, 48 ~ 50 (1970).
3. Diumycins A and B: Journal of Antibiotics, 22, 10, 490 ~ 493 (1969).
4. 19402RP Dutch Laid Open Patent No. 6802093 (1968).
5. Prasinomycins A, B and C Nature, 213, 1092 ~ 1094 (1967).
6. 8036RP South African Patent No. 65/6204 (1966).
7. 11837RP Abstract, The 9th International Congress for Microbiology, 165 (1966).

The production of pholipomycin will be fully disclosed hereunder by way of some representative examples. The production may be advantageously effected by various procedures depending upon the nature and properties as clarified according to this invention. Accordingly, the process for the production of pholipomycin is not restricted to the examples as given herein but the present process is contemplated to include all of those processes which enable to produce, extract and purify pholipomycin by the use of a pholipomycin-producing microorganism belonging to the genus Streptomyces and well-known procedures.

EXAMPLE 1

A culture medium having the following composition was employed.

| | | | |
|---|---|---|---|
| Glucose | 2.0 % | Meat extract | 0.5 % |
| Starch | 1.0 % | Calcium carbonate | 0.3 % |
| Baker's yeast | 0.9 % | Sodium chloride | 0.5 % |
| Polypepton | 0.5 % | | |

With 30 l each of the seed culture of strain 3176 which was cultivated on the above medium at 28°C. for 24 hours in a 100 l -volume tank, were inoculated two 600 l -volume fermentation tanks containing 300 l of the above medium (pH 7.2 before sterilization). Cultivation was effected at a temperature of 28 ± 1°C., 150 r.p.m. and aeration of 300 l/minute. After 114 hours was obtained the maximum production of pholipomycin.

640 l of the cultured broth so obtained was adjusted to pH 4.0 with sulfuric acid, 40 kg. of diatomaceous earth was added thereto and filtration was made by means of a filter press.

To the mycelial cake with the diatomaceous earth was added 300 l of anhydrous acetone to get an acetone concentration of 80 %, thereby pholipomycin being extracted. The extraction residue separated by a filter press was again extracted with 300 l of 80 % aqueous acetone. 580 l of the combined extracts (a pholipomycin content of 57.8 g.) was concentrated under reduced pressure to 60 l and, after distilling off the acetone, the residue was adjusted to pH 2.5 with sulfuric acid and extracted twice with 35 l portion of n-butanol.

The extract (56 l) was extracted twice with 37.5 l portion of 0.1 N aqueous ammonia, whereupon pholipomycin was transferred into the aqueous ammonia phase.

The extract (79 l) so obtained was concentrated under reduced pressure to 1.19 l (a content of pholipomycin 22.6 g., yield 39.1%).

The concentrate so obtained was adsorbed on a column packed with 3 l of Duolite A-2 (OH form) and, after washing with 6 l of water, pholipomycin was eluted with 0.1 N aqueous ammonia.

25.5 l of the so obtained active eluate was concentrated under reduced pressure to 1.62 l., which was then freeze-dried to obtain 26.2 g. of pholipomycin as crude powders. Purity 50.0 %, Yield 22.6 %.

EXAMPLE 2

A culture medium having the following composition was employed.

| | | | |
|---|---|---|---|
| Glucose | 4 % | $FeSO_4.7H_2O$ | 0.002 % |
| Meat extract | 0.2 % | $CuSO_4.7H_2O$ | 0.002 % |
| Soybean meal | 1.5 % | $AlCl_3.6H_2O$ | 0.002 % |
| $NaH_2PO_4$ | 0.05 % | $Na_2MoO_4.2H_2O$ | 0.002 % |
| $MgSO_4.7H_2O$ | 0.01 % | $CoSO_4.7H_2O$ | 0.002 % |
| $MnSO_4.7H_2O$ | 0.002 % | Cotton seed oil | 0.1 % |
| $ZnSO_4.7H_2O$ | 0.002 % | Adekanol LG126 (Asahi denka Kogyo K.K., antifoaming agent) | 0.002 % |

15 l of the above medium (pH 7.0 before sterilization) was charged into a 30 l -volume jar fermenter, the content was sterilized at 120°C. for 30 minutes and cooled. Then, 50 ml. of the seed culture of strain 3175, which was cultured on the same medium as above by charging 500 ml. of the medium into a 2 l -volume Erlenmyer flask and cultivating on a rotary shaker at 28°C. for 72 hours, was inoculated into the fermenter and cultivation was effected at a temperature of 28 ± 1°C., aeration of 20 l/minute, 135 r.p.m. and inner pressure 1.1 kg./cm². After 240 hours, was obtained the maximum production of pholipomycin of 150 μg./ml.

The cultured broth of 40 l combined from 3 jar fermenters was filterd with diatomaceous earth as a filter aid and washed with an equal volume of water.

8.5 kg. of the mycelial cake with diatomaceous earth was extracted three times with 75 % aqueous methanol to obtain 36 l of extract.

The extract was passed through a column packed with 1.9 l of Dowex 50W4 (H⁺ form), which was then washed with 70 % aqueous methanol to obtain a total volume of 40 l of the combined fluid. The fluid so obtained was passed through a column packed with 2 l of Duolite A-2 (acetic acid form), thereby pholipomycin being adsorbed thereon. The column was washed with 2 l of 70 % aqueous methanol and subsequently with 2 l of water and then eluted with 0.5 N aqueous ammonia.

2.49 l of the active eluate (activity yield of 58.5 %) was concentrated to dryness under reduced pressure and insoluble impurities were removed by the addition of methanol.

84 ml. of the fractions soluble in methanol was added dropwise to 2 l of acetone to precipitate pholipomycin. The so obtained precipitate was collected and dried under reduced pressure to give 12.7 g. of pholipomycin as crude powders (Purity 27.1 %, Yield 56.0 %).

The crude powder was dissolved in methanol, the resulting solution was adsorbed on a column packed with 160 ml. of Wakogel C-200 (Silica gel, manufactured by Wako Pure Chemical Industries Ltd., Japan) in chloroform-methanol (6:4). Impurities were removed with 3 l of chloroform-methanol (6:4) and pholipomycin was eluted with chloroform-methanol (5:5).

The activity of the eluates was monitored by a thin-layer chromatography to collect 4 l of those fractions having less impurities, which were concentrated to dryness to give 2.07 g. of pholipomycin (purity 75.8 %, yield 25.6 %) as crude powders.

The crude powders so obtained were dissolved in 9 ml. of water and adsorbed on a column of 200 ml. of DEAE cellulose (OH⁻ form). After washing with 1 l of aqueous ammonia at pH 9, elution was made with 0.01 N aqueous ammonia to collect 1.06 l of those active fractions, each providing a single spot on a thin-layer chromatography. The collected fractions were concentrated to dryness under reduced pressure to give 955 mg. of pholipomycin with a purity of 97.0 %. Yield 15.1 %. The product was dissolved in 5 ml. of methanol with heating and the resulting solution was cooled to separate the precipitate, which was then dried to give 474 mg. of pure pholipomycin. Yield 7.7 %.

The pholipomycin which may be produced by the abovementioned process is usable as growth promoting agents for animals.

As is explained hereinabove, pholipomycin has a potent antibacterial activity against bacteria and a utility for prevention and treatment of animal diseases caused by such bacteria. Additionally and more significantly, pholipomycin may be also effectively employed for the purpose of growth promotion of various animals. More specifically, where pholipomycin is orally administered to animals, growth of animals may be highly promoted, while its extremely low adsorption from the gastrointestinal tract and small retention of animal tissues are observed. This fact is believed to indicate almost complete lack of of pholipomycin in animal products such as eggs, meats and the like, which can provide a great advantage in an aspect of food hygiene.

The expression "Growth promotion of animals" means increase in body weight gain, improvement in food conversion rate, increase in egg-laying performance and the like.

The animals which are contemplated to be included herein and applicable with the present pholipomycin, are, for instance, domestic animals such as cattle, horse, swine, sheep, goat and the like; poultry such as fowl, turkey, duck and the like; pet animals such as dog, cat, small bird and the like.

For administration of pholipomycin may be preferably employed an oral route, but pholipomycin may also be administered in admixture with a feed or a drinkable water. Most preferably, pholipomycin may be administered in admixture with a feed. Where pholipomycin is to be employed as a feed additive, it may be admixed into a feed alone or in combination with an excipient with low toxicity; a nutrient supplement such as vitamins, minerals, amino acids and the like; an antibiotic substance such as macarbomycin, moenomycins and the like; an anticoccidial agent such as Beclothiamine, Amprolium, Buquinolate, Clopidol (3,5-dichloro-2,6-dimethyl-4-pyridinol) and the like; and an enzyme such as lysozyme and the like.

As a growth promoting agent, pholipomycin may be employed not only in a purified form but also as a cultured mycelium itself or in a crude form obtained at any optional stage during the extraction and purification thereof.

The amount of pholipomycin to be incorporated may be usually and preferably of 0.1 to 10 ppm (based on its activity) with respect to the feed, water or other bases to be added and the above-mentioned amount could not adversely affect the animals after a prolonged period of administration.

Then, a prominent growth promoting effect of this invention will be more fully illustrated by way of the following examples.

EXAMPLE 3

Effect on growth of broilers (Floor-pen test)

1. Chickens: Male and female small chickens of a broiler strain (GOTO 606), each group consisting of 15 chicken, were employed. After hatching, individual chicken with wing band was weighed.
2. Feeds: The main compositions of the feed used are summarized in Table 8. It is to be noted that the feed contains neither growth promoting agents nor antibiotic substances.

Table 8

| | |
|---|---|
| Yellow corn | 56.98 % |
| Fish meal | 10.00 % |
| Soybean meal | 24.00 % |
| Tallow fancy | 5.00 % |
| Alfalfa meal | 1.00 % |
| Minerals* | 2.17 % |
| Vitamin A | 20000IU/Kg |
| Vitamin $D_3$ | 4000ICU/Kg |
| Vitamin E | 100IU/Kg |
| Other vitamins** | 0.16 % |
| Methionine | 0.30 % |
| Lysine | 0.20 % |

Table 8-continued

| | |
|---|---|
| Ethoxyquin (Antioxidant) | 10 ppm |
| Beclothiamine (Anticoccidial agent) | 100 ppm |
| Clopidol (Anticoccidial agent) | 100 ppm |
| *Minerals (in 1 Kg. of feed) | |
| $CaCO_3$ | 8.0 g |
| $CaHPO_4.2H_2O$ | 6.0 g |
| NaCl | 5.0 g |
| $KH_2PO_4$ | 2.0 g |
| $MaSO_4$ | 55 mg |
| $MgSO_4$ | 500 mg |
| KI | 0.53 mg |
| $FeC_6H_5O_7 \cdot xH_2O$ | 80 mg |
| $CuSO_4.5H_2O$ | 4 mg |
| $5ZnO.2CO_3.4H_2O$ | 50 mg |
| $CoCl_2.6H_2O$ | 0.30 mg |
| **Other vitamins (in 1 Kg. of feed) | |
| Vitamin $B_1$ | 2.5 mg |
| Vitamin $B_2$ | 5.5 mg |
| Ca pantothenate | 9.3 mg |
| Niacin | 37.0 mg |
| Vitamin $B_6$ | 6.7 mg |
| Biotin | 0.09 mg |
| Choline chloride | 1000 mg |
| Inositol | 500 mg |
| Folic acid | 0.55 mg |
| Vitamin $K_1$ | 0.53 mg |
| Vitamin $B_{12}$ | 0.01 mg |

3. Concentration of pholipomycin to be incorporated: 2.5 ppm (based upon activity) of pholipomycin with a purity of 58.3 % was incorporated into the feed. A control without any pholipomycin was separately prepared.
4. Test method: Baby chickens were investigated about health condition and healthy chickens were weighed. Chickens were divided into several test groups without any difference about average body weight and continuously fed with broiler starter ration for one month. Each group consisted of 30 chickens, and each chicken was freely fed with the feed and drinkable water. Body weight of the chicken was measured every week and the feed intake was measured whenever a new feed was supplied.
5. Evaluation and Test results: Effect by the present pholipomycin was evaluated from body weight gain and feed conversion ratio.

Body weight gain (g.) = Final body weight − Initial body weight $$\text{Feed conversion ratio} = \frac{\text{Total feed ingestion}}{\text{Total body weight}}$$

Test results are summarized in Table 9.

Table 9

| | Pholipomycin group | Control |
|---|---|---|
| Average initial body weight (g.) | 39.0 ± 2.4* | 39.1 ± 2.6* |
| Average body weight gain (g.) | 560.6 ± 67.2* | 529.4 ± 62.5* |
| Feed conversion ratio | 1.77 | 1.92 |

*Standard deviation

As is apparent from the Table 9, a body weight gain effect is observed with improved feed conversion ratio in the pholipomycin group, as compared with the control.

EXAMPLE 4

Effect on growth of broilers (battery test)

Following the substantially same procedures and conditions as in the above Example except that crate fattening was effected, the test results in Table 10 were obtained. The crate fattening was effected by placing chicks in a brooder provided with an electrically heated wire floor and continuously feeding for 4 weeks.

Table 10

|  | Pholipomycin-group | Control |
|---|---|---|
| Average initial body weight (g.) | 37.6 ± 1.7* | 37.5 ± 2.1* |
| Average body weight gain (g.) | 490.6 ± 66.5* | 460.2 ± 56.5* |
| Feed conversion ratio | 1.61 | 1.65 |

*Standard deviation

EXAMPLE 5

Effect on growth of broilers (Field test)

1. Chickens: Chickens of Studler species from France were employed, each group consisting of 100 chickens without any sexing. After hatching, individual chicken with wing band was weighed.
2. Feeds: The rations used were commercially available ones (manufactured by Sumitomo Shiryo K.K., Japan), which contain no growth promoting agents and antibiotic substances.
3. Concentration of pholipomycin to be incorporated: 2.5 ppm (based upon activity) of pholipomycin with a purity of 50 % was incorporated into the feed. A control without any pholipomycin was separately prepared.
4. Test method: Chickens were fed in an umbrella-typed brooder capable of being heated with propane gas until 2 weeks old and continuously until 8 weeks old. The feed and drinkable water were freely supplied and both foul pox vaccine and Newcastle disease vaccine were inoculated during the test period, as commonly made.
5. Evaluation and Test results: Evaluation followed that in the above Example 3. The results are summarized in Table 11 wherein viability (%) means $$\frac{\text{Number of chickens surviving at the final weighing after initial weighing}}{\text{Number of chickens initially used}} \times 100$$

Table II

|  | Pholipomycin group | Control |
|---|---|---|
| Average initial body weight (g.) | 41.0 | 40.9 |
| Average body weight gain (g.) | 1989 ± 269* | 1896 ± 333* |
| Feed conversion ratio | 2.32 | 2.68 |
| Viability (%) | 99 | 94 |

*Standard deviation

As is apparent from the Table 11, not only improvement in body weight gain and feed conversion rate is accomplished but also rate of raising is highly improved.

EXAMPLE 6

Effect on growth of pigs (Field test)

First cross pigs (Hump × Rand) of 32 days old after birth were divided into two groups (Pholipomycin group and control) so that pigs in each group may have approximately equal average weights and numbers. Each group consisted of 8 pigs. Dosage (ppm) of pholipomycin are as follows:

|  | Latter term with synthetic | Feed for pig |
|---|---|---|
| Control | 0 | 0 |
| Pholipomycin-Group | 5 | 2 |

The feed employed was commercially available one without any growth promoting agent and antibiotic substance.

Body weight of the pig was weighed at a fixed time every 15 days and the feed intake was similarly measured.

Results:

Test results are summarized as follows:
1. Change in average body weight

|  | Synthetic milk period | | | Fattening (First period) | | |
|---|---|---|---|---|---|---|
| Week | Initial | 2 | 4 | 6 | 8 | 10 |
| Control | 8.5 | 14.6 | 19.6 | 25.3 | 33.0 | 48.9 |
| Pholipomycin-Group | 8.4 | 14.4 | 20.5 | 26.9 | 35.1 | 52.2 |

2. Body weight gain

|  | Synthetic milk period | | Fattening (First period) | | Total period | |
|---|---|---|---|---|---|---|
|  | B.W.G. | Index | B.W.G. | Index | B.W.G. | Index |
| Control | 11.1 | 100 | 23.6 | 100 | 34.7 | 100 |
| Pholipomycin-Group | 12.1 | 109 | 25.3 | 107 | 37.4 | 108 |

3. Feed intake and feed conversion ratio

|  | Synthetic milk period | | Fattening (First period) | |
|---|---|---|---|---|
|  | Intake | Feed Conv. | Intake | Feed Conv. |
| Control | 11.1 | 2.8 | 23.6 | 3.2 |
| Pholipomycin-Group | 12.1 | 2.6 | 25.3 | 2.9 |

It will be apparent from the above results that pholipomycin shows a prominent effect on promoting growth of pigs.

What is claimed is:

1. A method for growth promotion of animals which comprises administering to said animals an amount sufficient to promote growth of an animal of an antibiotic substance pholipomycin, said pholipomycin being a substance of an acidic white powder in a pure form, containing the following elements in the following proportions: C: 50.15%, H: 7.14%, N: 5.48%, P: 2.33%; having an empirical formula $C_{50\ 65}H_{85\ 111}N_{5\ 6}O_{25\ 35}P$; a molecular weight of 5100 by gel filtration; a melting point of 250°C. (with decomposition); a specific rotation in water of +6.0° at 20°C.; ultraviolet absorption spectrum maxima at 257 m$\mu$ (H$_2$O), 245 m$\mu$ (0.1N HCl) and 258 m$\mu$ (0.1N NaOH)

$E_{1cm}^{1\%}$ = 142 ($H_2O$), 93 (0.1N HCl) and 144 (0.1N HCl);

a pKa of 4.37; the following distinguishable bands in an infra-red absorption spectrum (in KBr) of 3500, 2980, 1740, 1650, 1565, 1410, 1390, 1340, 1240, 1080, 1050, 975, 950, 890, 860, 825, 805, 760, 670 $cm^{-1}$; being easily soluble in water, soluble in methanol and n-butanol, sparingly soluble in acetone, chloroform and ether; positive for Tollens reaction, false positive for Elson-Morgan reaction, negative for ninhydrin, Benedict, biuret, Bial, ferric chloride and anthrone reactions and stable at pH 4 ~ 10; and having Rf valves of 0.74 and 0.25 in cellulose and silica gel thin-layer chromatographies in n-propanol-$2NNH_4OH$ (7:3). ($H_2O$), 245 m$\mu$ 2. The method of claim 1, wherein the amount of said pholipomycin is from 0.1 to 10 ppm.

3. A growth promoting composition for animals which comprises a carrier and as an active ingredient an antibiotic substance pholipomycin at levels of 0.1 to 10 ppm, said pholipomycin being a substance of an acidic white powder in a pure form, containing the following elements in the following proportion C: 50.15 %, H: 7.14 %, N: 5.48 %, P: 2.33 %; having an empirical formula $C_{50 \sim 65} H_{85 \sim 111} N_{5 \sim 6} O_{25 \sim 35} P$, a molecular weight of 5100 by gel filtration, a melting point of 250°C. (with decomposition), a specific rotation in water of +6.0° at 20°C., ultraviolet absorption spectrum maxima at 257 m$\mu$ ($H_2O$), 245 m$\mu$ (0.1N HCl) and 258 m$\mu$ (0.1N NaOH)

$E_{1cm}^{1\%}$ = 142 ($H_2O$), 93 (0.1N HCl) and 144 (0.1N ECl), a pKa of 4.37, the following distinguishable bands in an infra-red absorption spectrum (in KBr) of 3500, 2980, 1740, 1650, 1565, 1410, 1390, 1340, 1240, 1080, 1050, 975, 950, 890, 860, 825, 805, 760, 670 $cm^{-1}$; being easily soluble in methanol and n-butanol, sparingly, soluble in acetone, chloroform and ether, positive for Tollens reaction, false positive for Elson-Morgan reaction, negative for ninhydrin, Benedict, biuret, Bial, ferric chloride and anthrone reactions and stable at pH 4 ~ 10; and having Rf values of 0.74 and 0.25 in cellulose and silica gel thin-layer chromatographies in n-propanol-$2NNH_4OH$ (7:3).

4. A poultry feed comprising a feed for poultry and from 0.1 to 10 ppm of the antibiotic substance pholipomycin defined in claim 3.

5. An animal feed comprising a feed for animals and from 0.1 to 10 ppm of the antibiotic substance pholipomycin defined in claim 3.

* * * * *